United States Patent [19]

Allen et al.

[11] Patent Number: 5,010,083

[45] Date of Patent: Apr. 23, 1991

[54] 2,6-METHANO-1,3-BENZODIAZOCINE COMPOUNDS WHICH HAVE USEFUL PHARMACEUTICAL UTILITY

[75] Inventors: Richard C. Allen, Flemington; Marc N. Agnew, Bridgewater, both of N.J.; David M. Fink, Doylestown, Pa.

[73] Assignee: Hoechst-Roussel Pharmaceuticals, Inc., Somerville, N.J.

[21] Appl. No.: 446,743

[22] Filed: Dec. 6, 1989

Related U.S. Application Data

[63] Continuation-in-part of Ser. No. 174,274, Mar. 28, 1988, abandoned.

[51] Int. Cl.[5] .................... A61K 31/44; C07D 471/06
[52] U.S. Cl. ....................................... 514/292; 546/81
[58] Field of Search ........................... 546/81; 514/292

[56] References Cited

U.S. PATENT DOCUMENTS 3,764,606 10/1973 Akkerman et al. .................. 546/97
3,932,422 1/1976 Michne ................................ 546/97

FOREIGN PATENT DOCUMENTS 4311470 5/1968 Japan .................................... 546/81

OTHER PUBLICATIONS

Kametani et al, *Chem. Pharm Bull*, 13, pp. 1220–1224 (1965).
Kametani et al, *Yakugaku Zassi*, 85, pp. 871–875 (1965).
Derwent Abstract, 85-064827/11 of Japan 60/019,767, 1/31/85.

*Primary Examiner*—Frederick E. Waddell
*Assistant Examiner*—Zinna Northington-Davis
*Attorney, Agent, or Firm*—Elliott Korsen

[57] ABSTRACT

Novel 2,6-methano-1,3-benzodiazocines, intermediates, processes for the preparation thereof, and methods for alleviating pain and for alleviating various memory dysfunctions characterized by a decreased cholinergic function, such as Alzheimer's disease, utilizing compounds or compositions thereof are disclosed.

32 Claims, No Drawings

2,6-METHANO-1,3-BENZODIAZOCINE COMPOUNDS WHICH HAVE USEFUL PHARMACEUTICAL UTILITY

This application is a continuation-in-part of pending U.S. application Ser. No. 174,274 filed Mar. 28, 1988, now abandoned.

This invention relates to 2,6-methano-1,3-benzodiazocines. More particularly, this invention relates to 2,6-methano-1,3-benzodiazocines of the formula

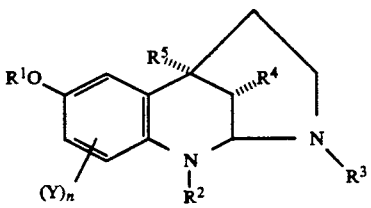

Formula I wherein $R^1$ is selected from the group consisting of hydrogen, loweralkyl, arylalkylaminocarbonyl loweralkylcarbonyl, loweralkylaminocarbonyl, cycloalkylaminocarbonyl, loweralkoxycarbonyl, aryloxycarbonyl, and arylaminocarbonyl; $R^2$ and $R^3$ are independently selected from the group consisting of hydrogen, loweralkyl, cycloalkylloweralkyl, arylloweralkyl, and loweralkenyl; $R^4$ and $R_5$ are independently hydrogen or loweralkyl; Y is halogen, loweralkyl, nitro, amino, loweralkylcarbonylamino, arylcarbonylamino, formyl or loweralkylaminocarbonyl; and n is an integer having a value of zero or 1; the geometrical isomers, optical antipodes or pharmaceutically acceptable acid addition salts thereof, which alone or in combination with inert adjuncts, are useful in alleviating pain and in alleviating various memory dysfunctions characterized by a decreased cholinergic function, such as Alzheimer's disease.

Of particular interest are 2,6-methano-1,3-benzodiazocines of the formula

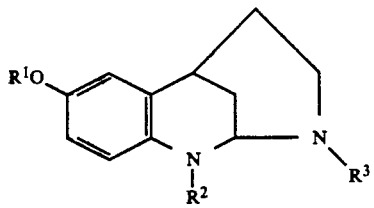

Formula II wherein $R^1$ is hydrogen or loweralkyl; and $R^2$ and $R^3$ are independently selected from the group consisting of hydrogen, loweralkyl, cycloalkylloweralkyl, and arylloweralkyl. Subgeneric to the 2,6-methano-1,3-benzodiazocines of this invention are Formula I compounds wherein:

(a) $R^1$ is hydrogen;
(b) $R^1$ is loweralkyl;
(c) $R^1$ is a group of the formula —C(O)$R^6$ wherein $R^6$ is selected from the group consisting of loweralkyl, loweralkylamino, cycloalkylamino, arylalkylamino and arylamino;
(d) $R^1$ is loweralkoxycarbonyl or aryloxycarbonyl;
(e) $R^2$ is hydrogen;
(f) $R^2$ is loweralkyl;
(g) $R^2$ is cycloalkylloweralkyl;
(h) $R^2$ is arylloweralkyl;
(i) $R^3$ is hydrogen;
(j) $R^3$ is loweralkyl;
(k) $R^3$ is arylloweralkyl;
(l) Y is chlorine or bromine;
(m) Y is amino or nitro;
(n) Y is loweralkylcarbonylamino or arylcarbonylamino;
(o) Y is formyl or loweralkylaminocarbonyl;
(p) n is zero; and
(q) n is 1.

In a further embodiment this invention relates to intermediates of the formula:

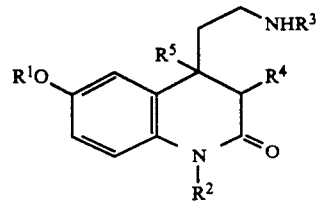

wherein $R^1$ is loweralkyl; $R^2$ and $R^3$ are independently hydrogen, loweralkyl, cycloalkylloweralkyl, loweralkenyl or arylloweralkyl; and $R^4$ and $R^5$ are independently hydrogen or loweralkyl.

As used throughout the specification and appended claims, the following definitions shall apply:

"Loweralkyl"—a linear or branched, acyclic hydrocarbon radical containing no unsaturation and having the formula —$C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like.

"Loweralkoxy"—an acyclic organic radical of the formula —$OC_xH_{2x+1}$ wherein x is an integer having a value of 1 to 7 inclusive, such as methoxy, ethoxy, 1- and 2-propoxy, 1,2-dimethylethoxy, 1-butoxy, 1- and 2-pentoxy, 3-hexoxy, 4-heptoxy, and the like.

"Loweralkenyl"—a linear or branched, acyclic hydrocarbon radical having one olefinic bond and represented by the formula —$C_xH_{2x-1}$ wherein x is an integer having a value of 3 to 7, inclusive, such as 2-propenyl, 3-butenyl, 3-pentenyl, 3-hexenyl, 6-heptenyl, and the like.

"Cycloalkyl"—a cyclic hydrocarbon radical of the formula —$C_xH_{2x-1}$ wherein x is an integer having a value of 3 to 7, inclusive, such as cyclopropyl, cyclobutyl, cyclopentyl, cyclohexyl, and cycloheptyl.

"Aryl"—a phenyl group optionally substituted by up to 3 substituents each of which is independently loweralkyl, loweralkoxy, halogen, trifluoromethyl, nitro or cyano. Unsubstituted and mono-substituted phenyl groups are preferred.

"Halogen"—a member of the group consisting of fluorine, chlorine, bromine, and iodine radicals.

"Arylloweralkyl"—a loweralkyl group having an aryl substituent thereon.

"Cycloalkylloweralkyl"—a loweralkyl group having a cycloalkyl substituent thereon.

"Loweralkylcarbonyl"—a group of the formula —C(O)$C_xH_{2x-1}$ wherein x is an integer having a value of 1 to 7 inclusive.

"Loweralkoxycarbonyl"—a group of the formula —C(O)OAlk wherein Alk is a loweralkyl substituent as previously defined.

"Amino"—a group of the formula —NH₂.

"Aminocarbonyl"—a group of the formula —C(O)NH₂.

"Loweralkylamino"—an amino group having a loweralkyl substituent thereon.

"Loweralkylaminocarbonyl"—an aminocarbonyl group substituted at the nitrogen atom thereof by a loweralkyl group.

"Loweralkylcarbonylamino"—a group of the formula —NHC(O)Alk wherein Alk is a loweralkyl substituent as previously defined.

"Cycloalkylamino"—an amino group having a cycloalkyl substituent thereon.

"Cycloalkylaminocarbonyl"—an aminocarbonyl group substituted at the nitrogen atom thereof by a cycloalkyl group.

"Arylamino"—an amino group having an aryl substituent thereon.

"Arylaminocarbonyl"—an aminocarbonyl group substituted at the nitrogen atom thereof by an aryl group.

"Arylcarbonylamino"—a group of the formula —NHC(O)Ar wherein Ar is an aryl substituent as previously defined.

"Aryloxycarbonyl"—a group of the formula —C(O)OAr wherein Ar is an aryl substituent as previously defined.

The 2,6-methano-1,3-benzodiazocines of this invention are synthesized by the processes illustrated in the Reaction Schemes which follow.

Reaction Scheme A details the preparation of an alkyl ester quinolinone 7. As illustrated, 5-hydroxy-2-nitrobenzaldehyde 1 is reacted with malonic acid to produce 3-(5-hydroxy-2-nitro)phenyl-2-propenoic acid 2 which is converted to 3-(5-methoxy-2-nitrophenyl)-2-propenoic acid methyl ester 3 and then reduced. The resulting aniline derivative 4 is then converted to a malonamide ester 5, which is cyclized to a quinolinone diester 6, and thereafter decarboxylated to the corresponding mono-ester derivative 7.

The reaction of 5-hydroxy-2-nitrobenzaldehyde 1 with malonic acid to produce propenoic acid 2 is known in the art. Typically the reaction is conducted in the presence of piperidine at from about room temperature to the reflux temperature of the solvent medium. See, for example, U.S. Pat. No. 4,424,150. The resulting acid 2 is converted to the ester 3 by treatment with dimethyl sulfate in the presence of an alkali metal carbonate (e.g. potassium carbonate, sodium carbonate, and the like; potassium carbonate being preferred). The esterification is ordinarily conducted in a non-reactive organic solvent such as, for example, acetone, 2-butanone or dimethylformamide, at from about room temperature to the reflux temperature of the solvent medium. Preferably, the reaction is conducted in acetone under reflux conditions. Reduction of the nitro group of the ester 3 to afford the aniline derivative 4 is accomplished by treatment with an appropriate reducing agent (e.g. dithionite, iron, zinc, and the like, or, aqueous titanium trichloride in the presence of ammonium acetate). Desirably, the reduction is carried out in the presence of a suitable organic solvent at a temperature of from about 0° C. to the reflux temperature of the reaction medium.

As further illustrated in Reaction Scheme A, loweralkyl functionality may be introduced at the 3-position of the propenoic acid ester 3 by converting the nitrobenzaldehyde 1 to the corresponding ketone 1a and thereafter proceeding with the reaction sequence previously described. Ketone formation may be effected by treating the nitrobenzaldehyde 1 with a Grignard reagent (e.g. methylmagnesium bromide, ethylmagnesium bromide, methylmagnesium chloride, ethylmagnesium chloride, and the like) to form an alcohol intermediate which is thereafter oxidized to the ketone 1a. The Grignard reaction is generally conducted at a temperature of from about 0° C. to about 100° C. under anhydrous conditions in the presence of a organic solvent. Suitable solvents include ethers such as dioxane, tetrahydrofuran, and the like. Oxidation of the alcohol intermediate may be accomplished by treatment with a suitable oxidizing agent, for example, pyridinium chlorochromate.

Conversion of the amino-substituted propenoic acid ester 4 to the malonamide ester 5 is accomplished by treatment with ethyl malonyl chloride in the presence of a suitable base (e.g. polyvinylpyridine, triethylamine, pyridine, and the like). The reaction is ordinarily carried out in a non-reactive organic solvent at a temperature of from about 0° C. to about 25° C., preferably at about 0° C. Among the suitable solvents there may be mentioned halocarbons such as, for example, dichloromethane, trichloromethane, 1,1-dichloroethane, 1,2-dichloroethane, and the like. Dichloromethane is the preferred solvent. Cyclization of the resulting malonamide ester 5 to the quinolinone diester 6 is achieved by reaction with an alkali metal alkoxide (e.g. sodium methoxide, sodium ethoxide, potassium methoxide, and the like; sodium methoxide being preferred) in the presence of a suitable alkanol (e.g. methanol, ethanol, n-butanol, and the like; methanol being preferred) at a temperature of from about 40° C. to the reflux temperature of the solvent medium. Preferably, reflux temperatures are employed in the cyclization reaction. Decarboxylation of the quinolinone diester 6 at temperatures of from about 150° C. to about 160° C. affords the mono-ester derivative 7. The decarboxylation is typically conducted in a wet dipolar aprotic organic solvent (e.g. hexamethylphosphoramide, dimethylsulfoxide, dimethylformamide, and the like) in the presence of an alkali metal halide (e.g. potassium chloride, sodium chloride, sodium bromide, and the like; sodium chloride being preferred).

Loweralkyl functionality can be introduced at the nitrogen atom of the mono-ester 7 by treatment with an alkali metal hydride (potassium hydride, sodium hydride, and the like; sodium hydride being preferred) followed by a loweralkyl halide (e.g. methyl bromide, methyl iodide, ethyl bromide, and the like) to afford the loweralkyl-substituted derivative 8. The alkylation is ordinarily conducted in the presence of a suitable solvent, (e.g. polar solvents such as, for example, dimethylformamide, hexamethylphosphoramide, dimethylsulfoxide, and the like; dimethylformamide being preferred), at temperatures of from about 0° C. to about 25° C.

Alternatively, substitution at the nitrogen atom of the quinolinone may be accomplished by prior alkylation of the aminophenyl-substituted derivative 4. Conversion of the resulting propenoic acid ester 4a to the malonamide ester 5a followed by cyclization to the diester 6a is as previously described. Treatment of the diester 6a with a suitable base (e.g. an alkali metal hydride such as sodium hydride), followed by alkylation with a lower alkyl halide (e.g. methyl iodide) gives the corresponding lower alkyl derivative 6b, which is decarboxylated as previously described to the quinolinone 8a.

As illustrated in Reaction Scheme B the parent system of the Formula I compounds of this invention i.e., a 2,6-methano-1,3-benzodiazocine 11 is produced by converting a 1-substituted quinoline 8a to an aldehyde derivative 9 which is reacted with a primary amine under reductive conditions to afford a 4-[(amino)ethyl]-2(1H)-quinolinone 10 and then cyclized to the benzodiazocine 11.

Conversion of the mono-ester derivative 8a to the corresponding aldehyde derivative 9 can be accomplished by treatment with a complex of sodium bis(2-methoxyethoxy)aluminum hydride and morpholine. The reaction is ordinarily conducted in the presence of a suitable solvent (e.g. aromatic hydrocarbons such as, for example, benzene, toluene, xylene, and the like; toluene being preferred) at a temperature of from about −25° C. to about 0° C., preferably from about −20° C. to about −25° C.

Alternatively, the aldehyde derivative 9 can be produced by reducing the ester 8a to an alcohol derivative 9a which is then oxidized to the aldehyde 9. Treatment of the ester 8a with an appropriate reducing agent, such as, for example, sodium bis(2-methoxyethoxy)aluminum hydride, lithium borohydride, and the like; lithium borohydride being preferred, provides a convenient means of forming the alcohol derivative 9a. The reduction is typically conducted in a non-reactive organic solvent, at a temperature of from about 25° C. to the reflux temperature of the solvent medium. Suitable solvents include ethereal solvents such as, for example, diethyl ether, dioxane, 1,2-dimethoxyethane, tetrahydrofuran, and the like; tetrahydrofuran being preferred. Oxidation of the alcohol derivative 9a to the aldehyde derivative 9 is accomplished by any of a number of synthetic procedures which are well known in the art. For example, treatment of the alcohol derivative 8a with a complex of chromium (VI) oxide and pyridine (i.e., $CrO_3 \cdot 2C_5H_5N$) at room temperature in a halogenated hydrocarbon such as methylene chloride or dichloroethane.

Reductive amination of the aldehyde derivative 9 is accomplished by treatment with a compound of the formula $R^3NH_2 \cdot HCl$ wherein $R^3$ is selected from the group consisting of loweralkyl, cycloalkylloweralkyl, and arylloweralkyl as previously described, and a suitable reducing agent (e.g. alkali metal cyanoborohydrides such as potassium cyanoborohydride, sodium cyanoborohydride, and the like; sodium cyanoborohydride being preferred). The reaction is generally conducted in an alkanol solvent (e.g. methanol, ethanol, n-butanol, and the like, methanol being preferred) at about room temperature. Cyclization of the amine 10 to the 8-methoxy-2,6-methano-1,3-benzodiazocine 11 is accomplished by treatment with an alkali metal (e.g. potassium, sodium, and the like; sodium being preferred). The cyclization is generally conducted in the presence of an alkanol solvent (e.g. methanol, ethanol, n-butanol, and the like, n-butanol being preferred) at reflux temperatures.

As illustrated in Reaction Scheme C the 2,6-methano-1,3-benzodiazocine 11 may be furnished with a variety of functional groups at the 8-position thereof. For example, conversion of the 8-methoxy-1,3-benzodiazocine 11 to the corresponding 8-hydroxy-substituted derivative 12 followed by treatment with an isocyanate of the formula $O=C=NR$ wherein R is loweralkyl, cycloalkyl, arylalkyl or aryl provides a 2,6-methano-1,3-benzodiazocine 13 wherein $R^1$ is loweralkylaminocarbonyl, cycloalkylaminocarbonyl, arylalkylaminocarbonyl or arylaminocarbonyl. Conversion of the 8-methoxy-2,6-methano-1,3-benzodiazocine 11 to the hydroxy-substituted derivative 12 can be accomplished by treatment with a dealkylating agent such as for example, boron tribromide, boron trichloride, aluminum chloride, and the like. In general, the dealkylation is conducted in the presence of a suitable solvent (e.g. a halogenated hydrocarbon such as chloroform, dichloromethane, and the like) at a temperature of from about −20° C. to about room temperature. Reaction of the hydroxy-substituted derivative 12 with an isocyanate is ordinarily carried out at temperatures of from about 0° C. to about 80° C. in an appropriate solvent (e.g. halogenated hydrocarbons such as chloroform). Alternatively, reaction of the phenol with 1,1'-carbonyldiimidazole, followed by addition of a primary or secondary amine of the formula $RNHR^7$, wherein R is as previously described and $R^7$ is hydrogen or loweralkyl provides the desired carbamates.

Alternatively, compounds where $R^1$ is loweralkylaminocarbonyl, arylalkylaminocarbonyl, cycloalkylaminocarbonyl or arylaminocarbonyl can be prepared in the following manner. The 8-hydroxy substituted derivative 12 is reacted with triisopropylsilyltrifluoromethane sulfonate and 2,6-lutidine to afford a silyl ether. To the silyl ether is added tetra-n-butyl ammonium fluoride solution and lithium chloride prior to the reaction with the isocyanate. The reaction is typically conducted at temperatures of from about 0° C. to room temperature in an appropriate solvent such as tetrahydrofuran.

Formula I compounds wherein $R^1$ is loweralkylcarbonyl are produced by reacting the 8-hydroxy-substituted derivative 12 with an anhydride of the formula $R^6C(O)OC(O)R^6$ (e.g., acetic anhydride). The acylation is generally conducted at a temperature of from about 0° C. to about 55° C., preferably from about 0° C. to about 30° C., in a halocarbon solvent (e.g., methylene chloride, dichloroethane, chloroform, and the like; methylene chllride being preferred). Desirably, the reaction is conducted in the presence of a suitable basic catalyst (e.g., N,N-dimethylaminopyridine, lutidine, collidine, and the like; N,N-dimethylaminopyridine being preferred).

Reaction of the 8-hydroxy-substituted derivative 12 with an alkyl- or aryl carbonate (e.g. methyl carbonate, phenyl carbonate, and the like) provides a means of furnishing a Formula I compound wherein $R^1$ is loweralkoxycarbonyl or aryloxycarbonyl. The reaction is ordinarily conducted in an ethereal solvent (tetrahydrofuran being preferred) in the presence of an alkali metal hydride such as, for example, sodium hydride, potassium hydride, and the like.

Reaction Scheme A
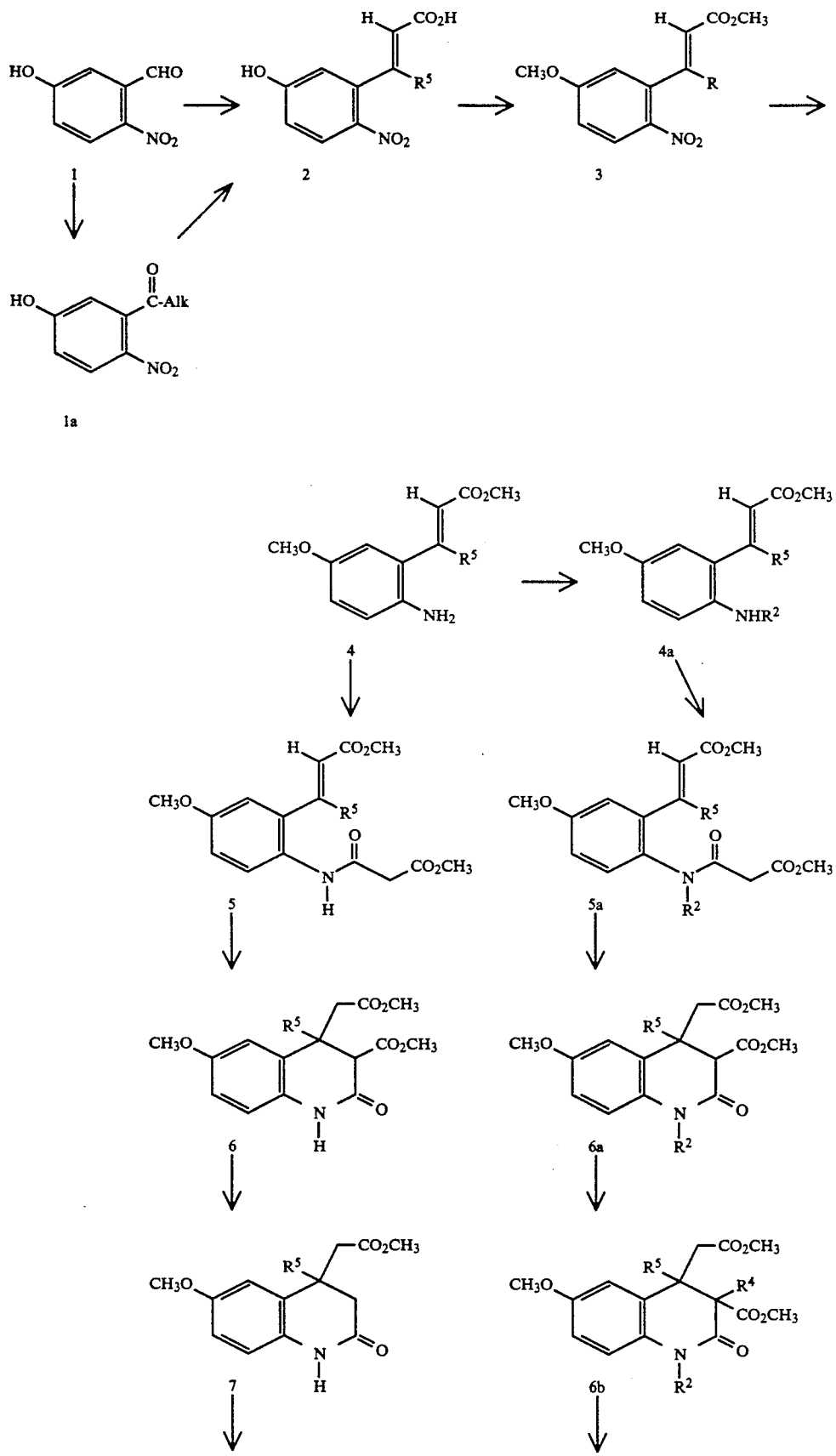

-continued
Reaction Scheme A

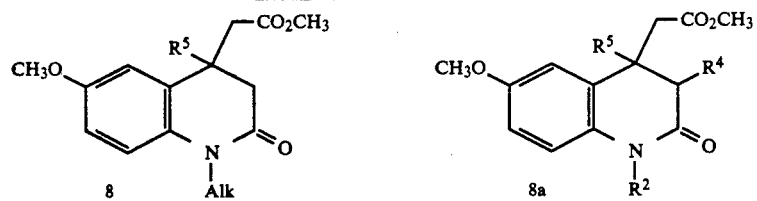

Wherein $R^2$ is loweralkyl, cycloalkylloweralkyl, arylloweralkyl or loweralkenyl, $R^4$ and $R^5$ are independently hydrogen or loweralkyl, and Alk is loweralkyl.

Reaction Scheme B

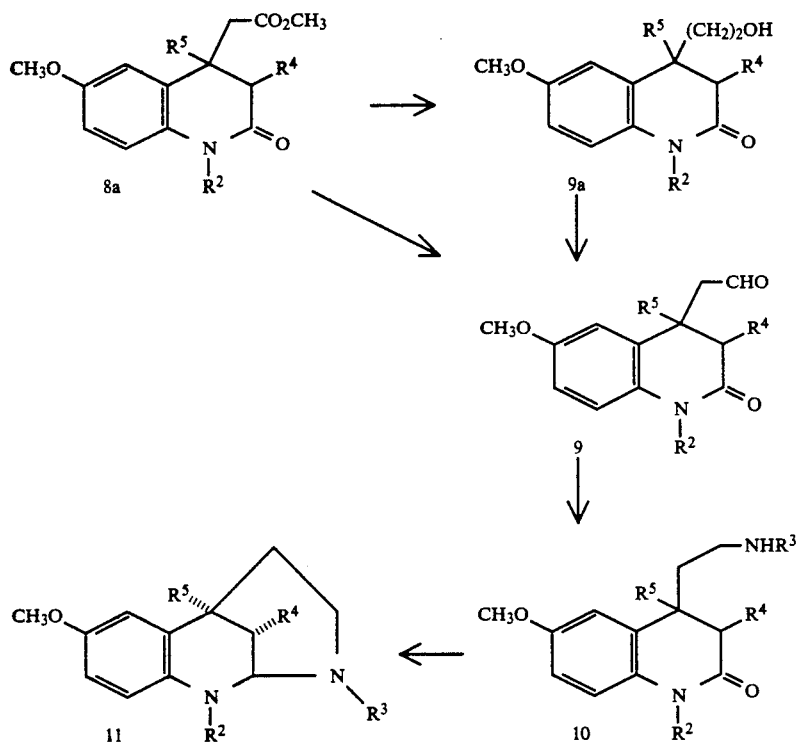

Wherein $R^2$ is loweralkyl, cycloalkylloweralkyl, arylloweralkyl or loweralkenyl and $R^3$, $R^4$ and $R^5$ are as herein described.

Reaction Scheme C

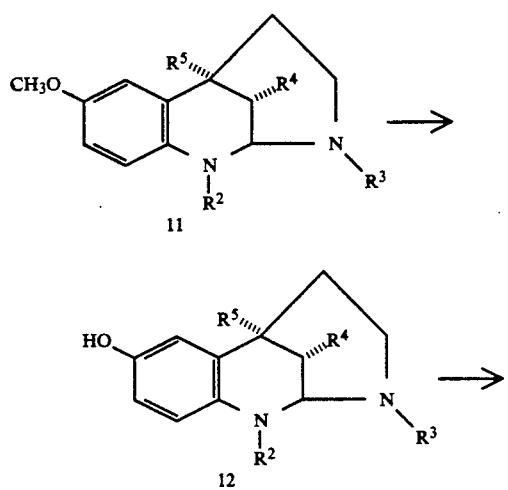

-continued
Reaction Scheme C

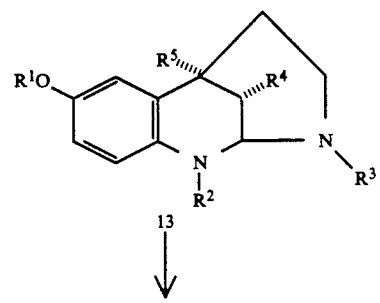

-continued
Reaction Scheme C

-continued
Reaction Scheme C

Wherein $R^1$, $R^2$, $R^3$, $R^4$, $R^5$, Y, and n are as herein described.

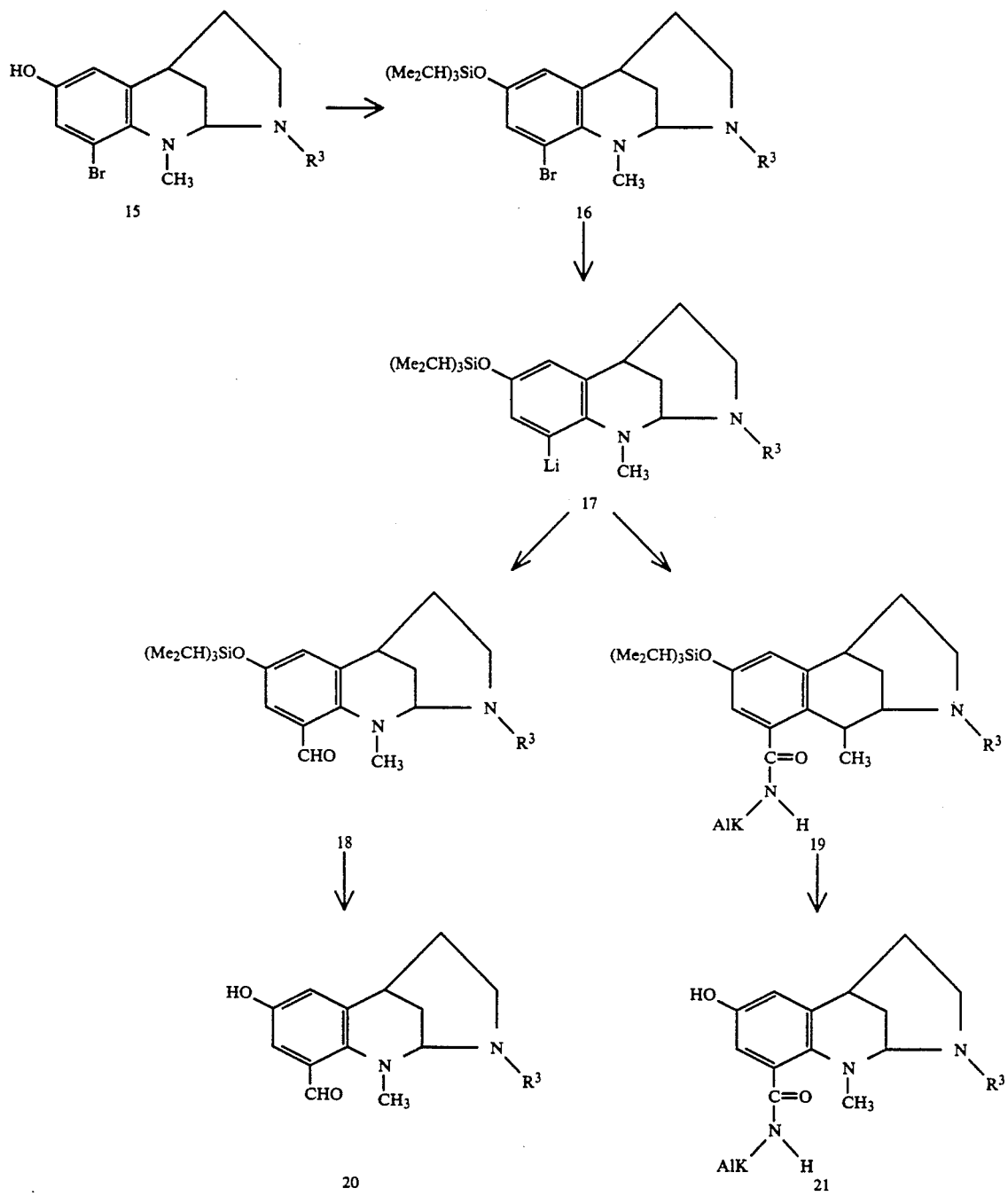

Wherein $R^3$ is as herein defined, Me is methyl, and Alk is loweralkyl.

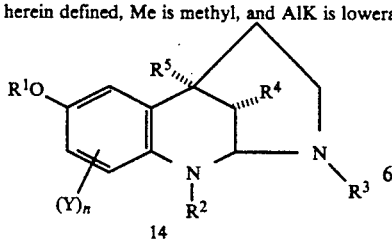

To provide a Formula I 2,6-methano-1,3-benzodiazocine wherein $R^1$ is loweralkyl (other than methyl), it is recommended that the 5-hydroxy-2-nitrobenzaldehyde 1 be reacted with a loweralkyl halide (e.g. isopropyl iodide, ethyl chloride, and the like) to form a 5-alkoxy-2-nitrobenzaldehyde which is then reacted as previously described to afford a 2,6-methano-1,3-benzodiazocine having an alkoxy group at the 8-position thereof.

The introduction of a substituent Y to the compounds of this invention may be effected by a variety of mechanisms tailored to the particular functional group involved. For example, the reaction of a 2,6-methano-1,3-benzodiazocine 13 with a halogenating agent (e.g. N-bromosuccinimide, N-chlorosuccinimide, and the like) is recommended as a means of forming a Formula I compound 14 wherein Y is halogen. Suggested solvents for the halogenation reaction include alkanols and halogenated hydrocarbons (e.g., methanol, chloroform, dichloroethane, and the like; methanol being preferred). Halogenation of an ester derivative of an 8-hydroxy-2,6-methano-1,3-benzodiazocine 12 followed by conversion of the halogenated ester to the corresponding 8-ol derivative, being a convenient means of directing halogenation at the 10-position of the compounds of this invention.

Treatment of an acetate or carbamate derivative of a benzodiazocine 13 with nitropyridium- or nitronium tetrafluoroborate in a suitable solvent (e.g. acetonitrile) provides as a means of furnishing Formula I compounds wherein Y is nitro. Reduction of the resultant nitro derivative affords the corresponding amine. Treatment of the amine with an acid anhydride (e.g. acetic anhydride, benzoic anhydride, and the like) and an appropriate acylation catalyst (e.g. 4-dimethylaminopyridine) is suggested as a means of forming loweralkylcarbonylamino or arylcarbonylamino derivatives 14.

To furnish a Formula I compound wherein Y is formyl or loweralkylaminocarbonyl, a 10-bromo-1,2,3,4,5,6-hexahydro-1-methyl-2,6-methano-1,3-benzodiazocin-8-ol 15 may be treated with triisopropylsilyl triflate to form a silyl ether derivative 16 which in turn is treated with an appropriate organolithium compound (e.g. t-butyl lithium) to afford an organolithium derivative 17 from which the desired formyl derivative 18 or loweralkylaminocarbonyl derivative 19 may be produced. See Reaction Scheme D.

The reaction of the 10-bromo-1,2,3,4,5,6-hexahydro-1-methyl-2,6-methano-1,3-benzodiazocin-8-ol 15 with triisopropyl triflate is typically conducted in a halogenated hydrocarbon solvent (dichloromethane being preferred) in the presence of 2,6-dimethylpyridine. The reaction is generally conducted at a temperature of from about 0° C. to about 25° C. Treatment of the silyl ether derivative 16 formed by this reaction with an organolithium derivative such as t-butyl lithium is generally conducted at reduced temperature in an ethereal solvent (e.g., tetrahydrofuran). Formyl and loweralkylaminocarbonyl derivatives are produced by treatment of the resultant organolithium derivative 17 with dimethylformamide or a loweralkylisocyanate respectively. Deprotection of the resultant formyl- and loweralkylaminocarbonyl substituted silyl ethers 18 and 19, such as by treatment with tetrabutylammonium fluoride, affords the corresponding phenols 20 and 21.

Included among the compounds of this invention are the following:

1,2,3,4,5,6-hexahydro-8-methoxy-2,6-methano-1,3-benzodiazocine;
1,2,3,4,5,6-hexahydro-1,3-dimethyl-2,6-methano-1,3-benzodiazocin-8-ol;
1,2,3,4,5,6-hexahydro-1,3-dimethyl-2,6-methano-1,3-benzodiazocin-8-ol, acetate;
1,2,3,4,5,6-hexahydro-1,3-dimethyl-2,6-methano-1,3-benzodiazocin-8-ol, methyl carbamate;
1,2,3,4,5,6-hexahydro-1,3-dimethyl-2,6-methano-1,3-benzodiazocin-8-ol, cyclopropyl carbamate;
1,2,3,4,5,6-hexahydro-1,3-dimethyl-2,6-methano-1,3-benzodiazocin-8-ol, phenyl carbamate;
1,2,3,4,5,6-hexahydro-1,3-dimethyl-2,6-methano-1,3-benzodiazocin-8-ol, 4-fluorophenyl carbamate;
3-benzyl-1,2,3,4,5,6-hexahydro-8-methoxy-1-methyl-2,6-methano-1,3-benzodiazocine;
3-(cyclopropylmethyl)-1,2,3,4,5,6-hexahydro-8-methoxy-1-methyl-2,6-methano-1,3-benzodiazocine;
1,2,3,4,5,6-hexahydro-8-methoxy-1-methyl-3-(3-methyl-2-butenyl)-2,6-methano-1,3-benzodiazocine;
1,2,3,4,5,6-hexahydro-8-methoxy-1,3,6,11-tetramethyl-2,6-methano-1,3-benzodiazocine;
9-chloro-1,2,3,4,5,6-hexahydro-8-methoxy-1,3-dimethyl-2,6-methano-1,3-benzodiazocine;
10-chloro-1,2,3,4,5,6-hexahydro-1,3-dimethyl-2,6-methano-1,3-benzodiazoin-8-ol;
9-bromo-1,2,3,4,5,6-hexahydro-1,3-dimethyl-2,6-methano-1,3-benzodiazocin-8-ol;
10-bromo-1,2,3,4,5,6-hexahydro-8-methoxy-1,3-dimethyl-2,6-methano-1,3-benzodiazocine;
10-bromo-1,2,3,4,5,6-hexahydro-1,3-dimethyl-2,6-methano-1,3-benzodiazocin-8-ol;
3-(cyclopropylmethyl)-1,2,3,4,5,6-hexahydro-1-methyl-2,6-methano-1,3-benzodiazocin-8-ol;
1,2,3,4,5,6-hexahydro-1-methyl-3-(2-phenylethyl)-2,6-methano-1,3-benzodiazocin-8-ol;
1,2,3,4,5,6-hexahydro-8-methoxy-1-methyl-3-(2-phenylethyl)-2,6-methano-1,3-benzodiazocine;
1,2,3,4,5,6-hexahydro-8-methoxy-1,3-dimethyl-10-nitro-2,6-methano-1,3-benzodiazocine;
10-amino-1,2,3,4,5,6-hexahydro-8-methoxy-1,3-dimethyl-2,6-methano-1,3-benzodiazocine;
10-formyl-1,2,3,4,5,6-hexahydro-1,3-dimethyl-2,6-methano-1,3-benzodiazocin-8-ol;
1,2,3,4,5,6-hexahydro-8-methoxy-1,3,10-trimethyl-2,6-methano-1,3-benzodiazocine;
1,2,3,4,5,6-hexahydro-1,3-dimethyl-10-(N-methylamino)carbonyl-2,6-methano-1,3-benzodiazocin-8-ol;
1,2,3,4,5,6-hexahydro-1,3-dimethyl-2,6-methano-1,3-benzodiazocin-8-ol, phenyl carbonate;
1,2,3,4,5,6-hexahydro-1,3-dimethyl-2,6-methano-1,3-benzodiazocin-8-ol, ethyl carbonate;
10-benzamido-1,2,3,4,5,6-hexahydro-8-methoxy-1,3-dimethyl-2,6-methano-1,3-benzodiazocine;
1,2,3,4,5,6-hexahydro-8-methoxy-1,3-dimethyl-2,6-methano-1,3-benzodiazocine; and
10-bromo-1,2,3,4,5,6-hexahydro-1,3-dimethyl-2,6-methano-1,3-benzodiazocin-8-ol acetate.

The 2,6-methano-1,3-benzodiazocines of this invention are useful as analgetics due to their ability to alleviate pain in mammals. The procedure employed to determine analgetic activity is a modification of the phenyl-p-quinone writhing assay in mice, a standard assay for analgesia [Proc. Soc. Exptl. Bio. Med., 95 729(1957)]. Pursuant to the modified procedure, phenyl-p-benzoquinone (Eastman, 12.5 mg) is dissolved in 5 ml of 95% ethanol and the solution is diluted to a total volume of 100 ml with distilled water. The solution is administered to the subject mice intraperitoneally at a dose of 10 ml per kg of body weight. A characteristic "writhe", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously or orally (p.o.) at 15, 30, 45, and 60 minutes prior to administration of the phenyl-p-quinone. A control group (2 animals per group) receive an equal volume of the vehicle. After the administration of the phenyl-p-quinone, the mice are placed separately in one liter beakers, and after five minutes, are observed for ten minutes. The number of writhes for each animal is recorded. The following formula is used to compute the percent inhibition:

$$\frac{\bar{x} \text{ Writhes in Control Group} - \bar{x} \text{ Writhes in Drug Group}}{\bar{x} \text{ Writhes in Control Group}} \times 100$$

The time period with the greatest percent of inhibition is considered the peak time. A dose range determination is generally reserved for those compounds which inhibit writhing by greater than 65-70% at the screening dose. A dose range determination is run in the same manner as the time response except 10 animals per group are tested at the peak time of test drug activity. Fifty animals, four test drug groups, and a vehicle control are employed. Animals are dosed and tested in a randomized manner. A calculated $ED_{50}$, i.e., the calculated dose at which 50% inhibition of writhing is produced, is determined by a computer linear regression analysis. The calculated subsutaneous (s.c.) dose effecting an approximately 50% inhibition of writhing ($ED_{50}$) in mice produced in this assay is as follows:

| Compound | Analgesic Activity (inhibition of Writhing) $ED_{50}$ mg/kg, s.c. |
|---|---|
| 1,2,3,4,5,6-hexahydro-8-methoxy-dimethyl-2,6-methano-1,3-benzodiazocine | 10.2 |
| 1,2,3,4,5,6-hexahycro-1,3-dimethyl-2,6-methano-1,3-benzodiazocin-8-ol | 0.70 |
| 1,2,4,5,6-hexahydro-1,3-dimethyl-2,6-methano-1,3-benzodiazocin-8-ol acetate | 0.74 |
| 10-bromo-1,2,3,4,5,6-hexahydro-1,3-dimethyl-2,6-methano-1,3-benzodiazocin-8-ol | 1.9 |
| pentazocine | 1.3 |

Analgesia production is achieved when the 2,6-methano-1,3-benzodiazocines of this invention are administered to a subject requiring such treatment as an effective oral, parenteral or intravenous dose of from 0.1 to 50 mg/kg of body weight per day. It is to be understood, however, that for any particular subject, specific dosage regimens should be adjusted according to the individual need and the professional judgment of the person administering or supervising the administration of the aforesaid compound. It is further understood that the dosages set forth herein are exemplary only and that they do not, to any extent, limit the scope or practice of the invention.

The compounds of the present invention are also useful in the treatment of various memory dysfunctions characterized by decreased cholinergic function, such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum cholinesterase) will give rise to fewer side effects and thus lower toxicity than physostigmine (an unspecific cholinesterase inhibitor). We have determined in vitro inhibition of acetylcholinesterase activity in rat striatum according to the method described below. Results of some of the compounds of this invention as well as those of physostigmine are presented below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells, AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents 1. 0.05M Phosphate buffer, pH 7.2
   (a) 6.85 g $NaH_2PO_4.H_2O$/100 ml distilled $H_2O$
   (b) 13.40 g $Na_2HPO_4.7H_2O$/100 ml distilled $H_2O$
   (c) add (a) to (b) until pH reaches 7.2
   (d) dilute 1:10
2. Chromogen-substrate buffer
   (a) 9.9 mg 5,5-dithiobisnitrobenzoic acid (DTNB) (0.25 mM)
   (b) 99 mg s-acetylthiocholine chloride (5 mM)
   (c) q.s. to 100 ml with 0.05M phosphate buffer, pH 7.2 (reagent 1)
3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine IC$_{50}$ determinations the Abbott Bichromatic Analyzer, ABA-100, is used to determine acetylcholinesterase activity.

Instrument settings
   Filter: 450-415
   Incubation temperature: 30° C.
   Decimal point: 0000
   Analysis time: 5 minutes
   Carousel Revolution: 3

| Reaction direction | down endpoint |
|---|---|

Syringe plate: 1:101 dilution

Following the 10 minuted preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with a Gilford 250 spectrophotometer. This method is used for more accurate kinetic measurements.

| Instrument settings | |
|---|---|
| Lamp: | visible |
| Filter: | no filter |
| Wavelength: | 412 nm |
| Slit width: | 0.2 mm |
| Selection: | small aperature |
| Calibrated absorbance: | 1.0 unit full scale |
| Chart speed: | 0.5 cm/min. |

Reagents are added to the reference and sample side of a split curvette as follows:

| Reference | Sample |
|---|---|
| 0.8 ml 0.05 M phosphate buffer | 0.8 ml 0.05 M phosphate buffer |
| 0.8 ml Chromogen-substrate buffer | 0.8 ml Chromogen-substrate buffer |
| | 10 microliter enzyme (tissue homogenate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula $$\text{rate (moles/liter/min)} = \text{slope}/(1.36 \times 10^4)$$

| Inhibition of Brain Acetycholinesterase Activity | |
|---|---|
| Compound | ($10^{-6}$ M Inhibitory Concentration) |
| 1,2,3,4,5,6-Hexahydro-1,3-dimethyl-2,6-methano-1,3-benzodiazocin-8-ol, cyclohexyl carbamate | 10.7 |
| 1,2,3,4,5,6-Hexahydro-1,3-dimethyl-2,6-methano-1,3-benzodiazocin-8-ol, methyl carbamate fumarate | .058 |
| [2S-[2b,6b]] and [2R-[2a,6a]]-1,2,3,4,5,6-Hexahydro-2,6-methano-1,3-benzodiazocin-8-ol, S-α-methylbenzylcarbamate salicylate | 8.7 |
| Tacrine (standard) | 5.7 |

2,6-Methano-1,3-benzodiazocines of this invention, while effective themselves, may be formulated and administered in the form of their pharmaceutically acceptable acid addition salts for purposes of stability, convenience, increased solubility and the like. Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit form is a capsule, it may contain, in addition to materials of the preceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or other sweetening agents, preservatives, dyes, coloring agents and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite, chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

The following examples are for illustrative purposes only and are not to be construed as limiting the invention. Unless otherwise indicated, with the exception of yields which are calculated on a molar basis, all parts and percentages provided in these Examples are by volume.

EXAMPLE 1

1,2,3,4,5,6-Hexahydro-8-methoxy-1,3-dimethyl-2,6-dimethyl-1,3-benzodiazocine

Step 1

To a stirred suspension of 172 g of potassium carbonate and 51.9 g of 3-(5-hydroxy-2-nitrophenyl)propenoic acid in 1.6 l of gently refluxing acetone was added, dropwise, 65.5 g of dimethylsulfate. The resulting mixture was refluxed overnight, cooled, filtered and concentrated. The concentrate was washed with cold methanol and dried to afford 3-(5-methoxy-2-nitrophenyl)-1-propenoic acid, methyl ester.

Step 2

To a stirred, chilled (ice bath) solution of 32.7 g of 3-(5-hydroxy-2-nitrophenyl)propenoic acid, methyl ester and 300 g of ammonium acetate in 700 ml of tetrahydrofuran was added 840 ml of titanium trichloride solution (20% in water). The resulting mixture was basified by the addition of about 1 kg of a 50% sodium hydroxide solution and diluted with ethyl acetate. The aqueous phase was separated and extracted with ethyl acetate. The combined organic phases were washed with saturated sodium chloride solution, dried over potassium carbonate, filtered, and concentrated to afford 3-(5-methoxy-2-aminophenyl)-1-propenoic acid, methyl ester.

Step 3

To a stirred, chilled (0° C.) suspension of 49.0 g of 3-(5-hydroxy-2-aminophenyl)propenoic acid, methyl ester and 47.4 g of polyvinylpyridine in 475 ml of dichloromethane was added, dropwise, 39.2 g of ethyl malonyl chloride. After stirring at 0° C. for 0.5 hour the mixture was filtered and concentrated to afford 3-[[2-[(methoxycarbonyl)ethenyl]-4-methoxyphenyl]amino]-3-oxopropanoic acid, ethyl ester.

Step 4

To a stirred, chilled (0° C.) suspension of crude 3-[[2-[(methoxycarbonyl)ethenyl]-4-methoxyphenyl]amino]-3-oxopropanoic acid, ethyl ester from step 3 in 700 ml of methanol was added, dropwise, a solution of 66.5 g of sodium methoxide (25% in methanol) in 250 ml of methanol. The resulting mixture was heated to reflux over 0.75 hour, cooled to 0° C., and poured into a cold saturated ammonium chloride solution. The aqueous layer was extracted with dichloromethane and the combined organic layers were washed with 10% hydrochloric acid solution and saturated sodium chloride solution, dried over anhydrous magnesium sulfate, filtered and concentrated to afford 1,2,3,4-tetrahydro-6-methoxy-3-(methoxycarbonyl)-2-oxo-4-quinoline acetic acid, methyl ester.

Step 5

A mixture of 67.0 g of 1,2,3,4-tetrahydro-6-methoxy-3-(methoxycarbonyl)-2-oxo-4-quinoline acetic acid, methyl ester and 13 g of sodium chloride in 23 ml of water and 300 ml of dimethyl sulfoxide was heated at 155° C. for 6 hours, cooled, and diluted with 1.2 l of a 1:1 mixture of ethyl acetate and water. The aqueous phase was separated and extracted with ethyl acetate, and the combined organic layers were washed with water and saturated sodium chloride solution, dried over anhydrous magnesium sulfate, filtered, and concentrated to afford 1,2,3,4-tetrahydro-6-methoxy-2-oxo-4-quinoline acetic acid, methyl ester.

Step 6

A solution of 40.8 g of 1,2,3,4-tetrahydro-6-methoxy-2-oxo-4-quinoline acetic acid, methyl ester in 500 ml of dimethyl formamide was added over 1 hour to a chilled (0° C.) suspension of 4.6 g of sodium hydride in 300 ml of dimethyl formamide. After stirring for 1 hour at ambient temperature, 27.5 g of methyl iodide was added and the mixture stirred for an additional hour. The mixture was then quenched with saturated ammonium chloride solution and extracted with ethyl acetate. The combined organic layers were washed with water and brine, dried over magnesium sulfate, filtered and concentrated to an oil. Column chromatography on silica gel (elution with hexane-ethyl acetate) afforded 1,2,3,4-tetrahydro-6-methoxy-1-methyl-2-oxo-4-quinoline acetic acid, methyl ester.

Step 7

Lithium borohydride (100 ml of a 2.0M solution in tetrahydrofuran) was added to a solution of 34.6 g of 1,2,3,4-tetrahydro-6-methoxy-1-methyl-2-oxo-4-quinoline acetic acid, methyl ester in 330 ml of tetrahydrofuran. The mixture was stirred at room temperature for 84 hours, cooled to 0° C., quenched with 10% aqueous hydrochloric acid, and concentrated. The aqueous layer was basified with potassium carbonate and extracted with ethyl acetate. The combined organic layers were washed with brine, dried over anhydrous magnesium sulfate, filtered and concentrated to afford 3,4-dihydro-4-(2-hydroxyethyl)-6-methoxy-1-methyl-2(1H)-quinolinone.

Step 8

To a chilled (0° C.) solution of 69 ml of pyridine in 600 ml of dichloromethane was added 42.5 g of chromium trioxide. The resulting mixture was stirred at room temperature for 0.5 hour and a solution of 10.0 g of 3,4-dihydro-4-(2-hydroxyethyl)-6-methoxy-1-methyl-2(1H)-quinolinone in 100 ml of dichloromethane was added, dropwise. The reaction mixture was stirred for 0.5 hour, the solvent was decanted, and the resulting residue washed with dichloromethane. The combined organic layers were washed with 5% sodium hydroxide solution, 10% hydrochloric acid solution, water, and brine, dried over anhydrous magnesium sulfate, filtered and concentrated. The resulting oil was filtered through silica (elution with ethyl acetate) and concentrated to afford 1,2,3,4-tetrahydro-6-methoxy-1-methyl-2-oxo-4-quinolineacetaldehyde.

Step 9

Sodium cyanoborohydride (1.2 g) was added to a solution of 10.0 g of methylamine hydrochloride and 4.6 g of 1,2,3,4-tetrahydro-6-methoxy-1-methyl-2-oxo-4-quinolineacetaldehyde in 142 ml of methanol. The solution was stirred at room temperature for 19 hours, quenched with 10% hydrochloric acid solution and extracted with ethyl acetate. The aqueous layer was basified with potassium hydroxide and the product extracted into ethyl acetate. The combined organic layers were washed with saturated sodium chloride solution, dried over anhydrous magnesium sulfate, filtered and concentrated to an oil. Column chromatography on silica gel (elution with triethylamine-methanol-ethyl acetate) afforded 3,4-dihydro-6-methoxy-1-methyl-4-[2-(methylamino)ethyl]-2(1H)-quinolinone as a solid. To a solution of the amine in methanol was added ethereal hydrochloric acid to pH 1. The solvent was removed, and the residue recrystallized from isopropanol-diethyl ether to afford the hydrochloride salt, m.p. 175°–177° C.

ANALYSIS: Calculated for $C_{14}H_{2}N_{20}O_{2} \cdot HCl$: 59.05% C, 7.43% H, 9.84% N. Found: 58.90% C, 7.38% H, 9.78% N.

Step 10

To a stirred solution of 4.50 g of 3,4-dihydro-6-methoxy-1-methyl-4-[2-(methylamino)ethyl]-2(1H)-quinolinone in 450 ml of refluxing n-butanol was added, incrementally over a period of 1.5 hours, 27.0 g of sodium. The resulting mixture was stirred at reflux until all of the sodium was consumed, and then it was cooled, and diluted with water. The aqueous phase was separated and extracted with ethyl acetate. The combined organic layers were washed with water and a saturated aqueous solution of sodium chloride, dried over magnesium sulfate, filtered, and concentrated. The concentrate was purified by means of column chromatography on silica gel (elution with triethylamine/methanol/ethyl acetate) followed by recrystallization from diethyl ether-pentane to afford 2.20 g (52%) of 1,2,3,4,5,6-hexahydro-8-methoxy-1,3-dimethyl-2,6-methano-1,3-benzodiazocine, m.p. 72°–73.5° C.

ANALYSIS: Calculated for $C_{14}H_{20}N_2O$: 72.38% C, 8.68% H, 12.05% N. Found: 72.30% C, 8.87% H, 12.16% N.

EXAMPLE 2

1,2,3,4,5,6-Hexahydro-8-methoxy-1-methyl-3-(1-phenylethyl)-2,6-methano-1,3-benzodiazocine fumarate 3,4-Dihydro-6-methoxy-1-methyl-4-[2-[(1-phenylethyl)amino]ethyl]-2(1H)-quinolinone was prepared in a manner similar to the procedure set forth in Steps 1 to 9 of Example 1.

To a stirred solution of 3.65 g of 3,4-dihydro-6-methoxy-1-methyl-4-[2-[(1-phenylethyl)amino]ethyl]-2(1H)-quinolinone in 270 ml of refluxing n-butanol was added, incrementally over a period of 1.5 hours, 7.40 g of sodium. The resulting mixture was stirred at reflux until all of the sodium was consumed, and then was cooled, and diluted with water. The aqueous phase was separated and extracted with ethyl acetate. The combined organic phase was washed with water and a saturated aqueous solution of sodium chloride, dried over anhydrous magnesium sulfate, filtered, and concentrated. The concentrate was purified by means of column chromatography on silica gel (elution with triethylamine/methanol/ethyl acetate) to afford 2.04 g (59%) of 1,2,3,4,5,6-hexahydro-8-methoxy-1-methyl-2-(1-phenylethyl)-2,6-methano-1,3-benzodiazocine as an oil.

To a solution of 1.83 g of the oil in diethyl ether was added 0.69 g of fumaric acid in methanol. The solvent was removed in vacuo, and the residual solid was recrystallized from methanol-diethyl ether to afford 1.96 g of 1,2,3,4,5,6-hexahydro-8-methoxy-1-methyl-3-(1-phenylethyl)-2,6-methano-1,3-benzodiazocine fumarate, m.p. 148°–151° C. (dec.).

ANALYSIS: Calculated for $C_{21}H_{26}N_2O$: 68.47% C, 6.89% H, 6.39% N. Found: 68.24% C, 6.89% H, 6.28% N.

EXAMPLE 3

1,2,3,4,5,6-Hexahydro-1,3-dimethyl-2,6-methano-1,3-benzodiazocin-8-ol fumarate

Boron tribromide solution (1.0M in dichloromethane, 0.10 mol, 100 ml) was added dropwise over one hour to a chilled (−78° C.) degassed solution of 7.45 g of 1,2,3,4,5,6-hexahydro-8-methoxy-1,3-dimethyl-2,6-methano-1,3-benzodiazocine in 220 ml of dichloromethane. The reaction mixture was warmed to 0° C. over one hour and then stirred at 0° C. for an additional hour. The mixture was then quenched with a saturated aqueous solution of sodium carbonate. The aqueous layer was further basified with potassium carbonate and the product extracted into dichloromethane. The combined organic layers were washed with a saturated aqueous solution of sodium chloride, dried over potassium carbonate, filtered, and concentrated to afford 5.68 g of 1,2,3,4,5,6-hexahydro-1,3-dimethyl-2,6-methano-1,3-benzodiazocin-8-ol, as a solid.

The solid was suspended in 25 ml of methanol and treated with a solution of 3.3 g of fumaric acid in 25 ml of hot methanol to precipitate the corresponding fumarate salt. Trituration of the precipitate with hot methanol afforded 4.3 g of 1,2,3,4,5,6-hexahydro-1,3-dimethyl-2,6-methano-1,3-benzodiazocin-8-ol fumarate, m.p. 160°–166° C. (dec).

ANALYSIS: Calculated for $C_{13}H_{18}N_2O \cdot C_4H_4O_4$: 61.07% C, 6.63% H, 8.38% N. Found: 60.82% C, 6.69% H, 8.26% N.

EXAMPLE 4

3-(Cyclopropylmethyl)-1,2,3,4,5,6-hexahydro-8-methoxy-1-methyl-2,6-methano-1,3-benzodiazocine 4-[2-[(Cyclopropylmethyl)amino]ethyl]-3,4-dihydro-6-methoxy-1-methyl-2(1H)-quinolinone was prepared in a manner similar to the procedure set forth in steps 1 to 9 of Example 1.

To a stirred solution to 5.3 g of 4,[2-[(cyclopropylmethyl)amino]-3,4-dihydro-6-methoxy-1-methyl-2(1H)quinolinone in 400 ml of refluxing n-butanol was added, incrementally over a period of one hour, 12.7 g of sodium. The resulting mixture was stirred at reflux until all of the sodium was consumed, and then was cooled and diluted with water. The aqueous phase was separated and extracted with ethyl acetate. The combined organic phase was washed with water and a saturated aqueous solution of sodium chloride, dried over anhydrous magnesium sulfate, filtered and concentrated. The concentrate was purified by means of column chromatography on silica gel (elution with triethylamine/hexane/ethyl acetate) to afford 3-(cyclopropylmethyl)-1,2,3,4,5,6-hexahydro-8-methoxy-1-methyl-2,6-methano-1,3-benzodiazocine as an oil. Kugelhrohr distillation of the oil afforded 2.2 g of analytically pure product.

ANALYSIS: Calculated for $C_{17}H_{24}N_2O$: 74.96% C, 8.88% H, 10.28% N. Found: 74.79% C, 8.82% H, 10.08% N.

EXAMPLE 5

1,2,3,4,5,6-Hexahydro-1,3-dimethyl-2,6-methano-1,3-benzodiazocin-8-ol acetate, fumarate A catalytic amount, (0.019 g) of N,N-dimethylaminopyridine was added to a deoxygenated solution of 5.8 g of 1,2,3,4,5,6-hexahydro-1,3-dimethyl-2,6-methano-1,3-benzodiazocin-8-ol and 5.4 g of acetic anhydride in 270 ml of dichloromethane. After stirring for 15 minutes, the reaction mixture was treated with a saturated sodium bicarbonate solution. The aqueous layer was separated and extracted with dichloromethane. The combined organic layers were washed with saturated sodium chloride solution, dried over anhydrous magnesium sulfate, filtered and concentrated to an oil (7.1 g). Column chloromatography of a 3.5 g aliquot of the oil (silica gel; elution with triethylamine-methanol-ethyl acetate) afforded 2.2 g of 1,2,3,4,5,6-hexahydro-1,3-dimethyl-2,6-methano-1,3-benzodiazocin-8-ol acetate as a solid.

The solid product was dissolved in hot methanol, treated with fumaric acid (1.08 g) and concentrated. Treatment of the concentrate with diethyl ether precipitated 2.5 g of the corresponding fumarate, m.p. 183°-184° C. (dec.).

ANALYSIS: Calculated for $C_{15}H_{20}N_2O_2.C_4H_4O_4$: 60.63% C, 6.43% H, 7.44% N. Found: 60.51% C, 6.47% H, 7.47% N.

EXAMPLE 6

10-Bromo-1,2,3,4,5,6-hexahydro-1,3-dimethyl-2,6-methano-1,3-benzodiazocin-8-ol acetate, salicylate N-Bromosuccinimide (2.40 g) was added in three portions to a solution of 3.50 g of crude 1,2,3,4,5,6-hexahydro-1,3-dimethyl-2,6-methano-1,3-benzodiazocin-8-ol acetate in 135 ml of deoxygenated methanol. The resulting solution was stirred at room temperature for five minutes and then diluted with dichloromethane and a saturated sodium bicarbonate solution. The aqueous phase was separated and extracted with dichloromethane, and the combined organic layers were washed with saturated sodium chloride solution, dried over anhydrous magnesium sulfate, filtered, and concentrated to an oil. Column chromatography of the oil (silica gel elution with triethylamine-methanol-ethyl acetate) afforded 1.80 g (33%) of 10-bromo-1,2,3,4,5,6-hexahydro-1,3-dimethyl-2,6-methano-1,3-benzodiazocine-8-ol acetate as a solid.

The solid product was dissolved in methanol and treated with 0.72 g of salicyclic acid in diethyl ether. Concentration afforded a foam, which was crystallized from dichloromethane-pentane and then recrystallized from methanol to provide 1.24 g of 10-bromo-1,2,3,4,5,6-hexahydro-1,3-dimethyl-2,6-methano-1,3-benzodiazocin-8-ol acetate, salicylate, m.p. 168°-169° C.

ANALYSIS: Calculated for $C_{15}H_{19}BrN_2O_2.C_7H_6O_3$: 55.36% C, 5.28% H, 5.87% N. Found: 55.45% C, 5.24% H, 5.81% N.

EXAMPLE 7

10-Bromo-1,2,3,4,5,6-hexahydro-1,3-dimethyl-2,6-methano-1,3-benzodiazocin-8-ol, hemi-fumarate A deoxygenated suspension of 3.59 g of 10-bromo-1,2,3,4,5,6-hexahydro-1,3-dimethyl-2,6-methano-1,3-benzodiazocin-8-ol acetate and 2.90 g of potassium carbonate in 50 ml of 20% aqueous methanol was stirred at ambient temeprature for 15 minutes and then diluted with water and dichloromethane. The aqueous layer was separated and extracted with dichloromethane. The combined organic phases were washed with saturated sodium chloride solution, dried over potassium carbonate, filtered and concentrated. The concentrate was suspended in 30 ml of methanol, treated with a solution of 0.87 g of fumaric acid in 25 ml of hot methanol, and heated briefly. Cooling to ambient temperature precipitated 1.2 g (32%) of 10-bromo-1,2,3,4,5,6-hexahydro-1,3-dimethyl-2,6-methano-1,3-benzodiazodin-8-ol, hemi-fumarate, m.p. 195°-200° (dec.).

ANALYSIS: Calculated for $C_{13}H_{17}N_2O.\frac{1}{2}C_4H_4O_4$: 50.72% C, 5.39% H, 7.89% N. Found: 50.61% C, 5.44% H, 7.89% N.

EXAMPLE 8

1,2,3,4,5,6-Hexahydro-1,3-dimethyl-2,6-methano-1,3-benzodiazocin-8-ol, cyclohexyl carbamate Triisopropylsilyltrifluoromethane sulfonate (9.90 g) was added dropwise to a 0° C. deoxygenated solution of 2,6-lutidene (6.66 g) and 1,2,3,4,5,6-hexahydro-1,3-dimethyl-2,6-methano-1,3-benzodiazocin-8-ol (5.43 g) in dichloromethane under nitrogen. The resulting solution was stirred at 0° C. for 3 hours, and then it was diluted with water and extracted into dichloromethane. The combined organic layers were washed with brine, dried over magnesium sulfate, filtered, and concentrated to afford 12.1 of an oil. Column chromatography on silica gel (elution with triethylamine-methanol-ethyl acetate) afforded 5.5 g of the desired silyl ether.

To the above silyl ether (2.5 g) in 67 mol of tetrahydrofuran at room temperature was added tetra-n-butyl ammonium fluoride solution (1M in tetrahydrofuran, 6.68 ml). The resulting solution was stirred at room temperature for 15 min., and then lithium chloride (2.8 g) was added and the mixture stirred for 5 minutes as the lithium chloride dissolved. Cyclohexyl isocyanate (0.91 g) was added to the above solution, and the mixture was stirred for 18 hours, then quenched with water. The layers were separated and the aqueous phase was extracted with dichloromethane. The combined organic layers were washed with saturated sodium chloride solution, dried over magnesium sulfate, filtered and concentrated to afford 2.2 g of crude product. Column chromatography on silica gel (elution with triethylamine-methanol-ethyl acetate) provided 1.36 g of a foam. This sample was combined with an additional 0.8 g of product and chromatographed on alumina (elution with triethylamine-ethyl acetate) to give 2.02 g of 1,2,3,4,5,6-hexahydro-1,3-dimethyl-2,6-methano-1,3-benzodrazocin-8-ol, cyclohexyl carbamate as a foam, m.p. 50°-60° C.

ANALYSIS: Calculated for $C_{20}H_{29}N_3O_2$: 69.94% C, 8.51% H, 12.23% N. Found: 69.35% C, 8.69% H, 11.64% N.

EXAMPLE 9

1,2,3,4,5,6-Hexahydro-1,3-dimethyl-2,6-methano-1,3-benzodiazocin-8-ol, methyl carbamate fumarate Triisopropylsilyltrifluoromethane sulfonate (9.90 g) was added dropwise to a 0° C. deoxygenated solution of 2,6-lutidene (6.66 g) and 1,2,3,4,5,6-hexahydro-1,3-dimethyl-2,6-methano-1,3-benzodiazocin-8-ol (5.43 g) in dichloromethane under nitrogen. The resulting solution was stirred at 0° C. for 3 hours, and then it was diluted with water and extracted into dichloromethane. The combined organic layers were washed with brine, dried over magnesium sulfate, filtered, and concentrated to afford 12.1 g of an oil. Column chromatography on silica gel (elution with triethylamine-methanol-ethyl acetate) afforded 5.6 g of the desired silyl ether.

To the above silyl ether (2.4 g) in 64 m of tetrahydrofuran at room temperature was added tetra-n-butyl ammonium fluoride solution (1M in tetrahydrofuran, 6.4 ml). The resulting solution was stirred at room temperature for 15 minutes and then lithium chloride (2.7 g) was added, and the mixture stirred for 5 minutes as the lithium chloride dissolved. Methyl isocyanate (0.39 g) was added to the above solution, and the mixture was stirred for 18 hours then quenched with water. The layers were separated and the aqueous phase was extracted with dichloromethane. The combined organic layers were washed with saturated sodium chloride solution, dried over magnesium sulfate, filtered, and concentrated to afford 2.2 g of crude product. Column chromatography on silica gel (elution with triethylamine-methanol-ethyl acetate) provided 0.75 g of a foam.

The carbamate was dissolved in hot methanol and 0.316 g of fumaric acid were added. Diethyl ether was then added and the mixture was allowed to cool. Filtration afforded 700 mg of a solid which was recrystallized from methanol-diethyl ether, affording 0.45 g of 1,2,3,4,5,6-hexahydro-1,3-dimethyl-2,6-methano-1,3-benzodiazocin-8-ol methyl carbamate fumarate.

ANALYSIS: Calculated for $C_{19}H_{25}N_3O_6$: 58.30% C, 6.44% H, 10.73% N. Found: 58.42% C, 6.75% H, 10.59% N.

EXAMPLE 10

[2S-[2b,6b]] and [2R-[2a,6a]]-1,2,3,4,5,6-Hexahydro-2,6-methano-1,3-benzodiazocin-8-ol, S-α-methylbenzylcarbamate salicylate Triisopropylsilyltrifluoromethane sulfonate (10.5 g) was added dropwise to a 0° C. deoxygenated solution of 2,6-lutidene (7.06 g) and 1,2,3,4,5,6-hexahydro-1,3-dimethyl-2,6-methano-1,3-benzodiazocin-8-ol (5.75 g) in dichloromethane (130 ml) under nitrogen. The resulting solution was stirred at 0° C. for 3 hours, and then it was diluted with water and extracted into dichloromethane. The combined organic layers were washed with brine, dried over magnesium sulfate, filtered, and concentrated to afford 14.5 g of an oil. Column chromatography on silica gel (elution with triethylamine-methanol-ethyl acetate) afforded 7.1 g of the desired silyl ether.

To the above silyl ether (6.63 g) in 75 ml of tetrahydrofuran at room temperature was added tetra-n-butyl ammonium fluoride solution (1M in tetrahydrofuran, 17.7 ml). The resulting solution was stirred at room temperature for 15 minutes, and then lithium chloride (7.5 g) was added, and the mixture was stirred for 5 minutes as the lithium chloride dissolved. S-α-methylbenzylisocyanate (3.0 g) was added to the above solution, and the mixture was stirred for 18 hours, then quenched with water. The layers were separated, and the aqueous phase was extracted with dichloromethane. The combined organic layers were washed with saturated sodium chloride solution, dried over magnesium sulfate, filtered and concentrated to afford 9.5 g of crude product. The oil was chromatographed twice (silica gel, elution with triethylamine-methanol-ethyl acetate) to afford 3.5 g of the desired product as a foam. Treatment of the foam in diethyl ether with an equivalent amount of salicyclic acid in diethyl ether precipitated 3.1 g of [2S-[2b,6b]] and [2R-[2a,6a]]-1,2,3,4,5,6-Hexahydro-2,6-methano-1,3-benzodiazocin-8-ol, S-α-methylbenzylcarbamate salicylate, m.p. 95°-100° C.

ANALYSIS: Calculated for $C_{29}H_{33}N_3O_5$: 69.17% C, 6.61% H, 8.34% N. Found: 68.57% C, 6.50% H, 8.40% N.

What is claimed is:

1. A compound of the formula:

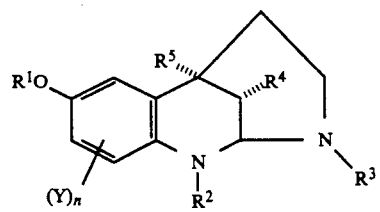

wherein $R^1$ is selected from the group consisting of hydrogen, loweralkyl, loweralkylcarbonyl, loweralkylaminocarbonyl, cycloalkylaminocarbonyl, arylalkylaminocarbonyl, loweralkoxycarbonyl, aryloxycarbonyl, and arylaminocarbonyl; $R^2$ and $R^3$ are independently selected from the group consisting of hydrogen, loweralkyl, cycloalkylloweralkyl, arylloweralkyl, and loweralkenyl; $R^4$ and $R^5$ are independently hydrogen or loweralkyl; Y is halogen, loweralkyl, nitro, amino, loweralkylcarbonylamino, arylcarbonylamino, formyl or loweralkylaminocarbonyl; the term aryl signifying a phenyl group optionally substituted by up to 3 substituents each of which is independently loweralkyl, loweralkoxy, halogen, trifluoromethyl, nitro or cyano; the term cycloalkyl signifying a cyclic hydrocarbon radical of the formula $-C_xH_{2x-1}$, wherein X is an integer having a value of 3 to 7, inclusive; and n is an integer having a value of zero or 1; or a geometrical isomer, optical antipode or a pharmaceutically acceptable acid addition salt thereof.

2. A compound as defined in claim 1 wherein n is zero, and $R^2$ and $R^3$ are independently selected from the group consisting of hydrogen, loweralkyl, cycloalkylloweralkyl, and arylloweralkyl.

3. A compound as defined in claim 2 wherein $R^1$ is hydrogen or loweralkyl.

4. A compound as defined in claim 3 wherein $R^2$ is loweralkyl.

5. A compound as defined in claim 4 wherein $R^3$ is loweralkyl.

6. A compound as defined in claim 4 wherein $R^3$ is arylloweralkyl.

7. A compound as defined in claim 5 wherein $R^4$ and $R^5$ are hydrogen.

8. A compound as defined in claim 2 wherein $R^1$ is loweralkoxycarbonyl or aryloxycarbonyl.

9. A compound as defined in claim 2 wherein $R^1$ is a group of the formula —C(O)$R^6$ wherein $R^6$ is selected from the group consisting of loweralkyl, loweralkylamino, arylalkylamino, cycloalkylamino, and arylamino.

10. The compound of claim 5 which is 1,2,3,4,5,6-hexahydro-8-methoxy-1,3-dimethyl-2,6-methano-1,3-benzodiazocine.

11. The compound of claim 6 which is 1,2,3,4,5,6-hexahydro-8-methoxy-1-methyl-3-(1-phenylethyl)-2,6-methano-1,3-benzodiazocine.

12. A compound as defined in claim 4 wherein $R^3$ is cycloalkylloweralkyl.

13. The compound of claim 12 which is 3-(cyclopropylmethyl)-1,2,3,4,5,6-hexahydro-8-methoxy-1-methyl-2,6-methano-1,3-benzodiazocine.

14. A compound as defined in claim 2 wherein $R^1$ is hydrogen.

15. A compound as defined in claim 14 wherein $R^2$ and $R^3$ are loweralkyl.

16. The compound of claim 15 which is 1,2,3,4,5,6-hexahydro-1,3-dimethyl-2,6-methano-1,3-benzodiazocin-8-ol.

17. A compound as defined in claim 9 wherein $R^2$ and $R^3$ are loweralkyl.

18. The compound of claim 17 which is 1,2,3,4,5,6-hexahydro-1,3-dimethyl-2,6-methano-1,3-benzodiazocin-8-ol acetate.

19. A compound as defined in claim 1 wherein n is 1.

20. A compound as defined in claim 19 wherein $R^2$ and $R^3$ are loweralkyl.

21. A compound as defined in claim 20 wherein Y is chlorine or bromine.

22. A compound as defined in claim 21 wherein $R^1$ is hydrogen.

23. The compound of claim 22 which is 10-bromo-1,2,3,4,5,6-hexahydro-1,3-dimethyl-2,6-methano-1,3-benzodiazocin-8-ol.

24. A compound as defined in claim 21 wherein $R^1$ is a group of the formula —C(O)$R^6$ wherein $R^6$ is selected from the group consisting of loweralkyl, loweralkylamino, cycloalkylamino, and arylamino.

25. The compound of claim 24 which is 10-bromo-1,2,3,4,5,6-hexahydro-1,3-dimethyl-2,6-methano-1,3-benzodiazocin-8-ol acetate.

26. A pharmaceutical composition comprising an effective pain alleviating amount of a compound as defined in claim 1 and suitable carrier therefor.

27. A method of treating a patient in need of relief from pain which comprises administering to the patient an effective amount of a compound as defined in claim 1.

28. The compound as defined in claim 1 which is 1,2,3,4,5,6-hexahydro-1,3-dimethyl-2,6-methano-1,3-benzodiazocin-8-ol, cyclohexyl carbamate.

29. The compound as defined in claim 1 which is 1,2,3,4,5,6-hexahydro-1,3-dimethyl-2,6-methano-1,3-benzodiazocin-8-ol, methyl carbamate fumarate.

30. The compound as defined in claim 1 which is [2S-[2b,6b]] and [2R-[2a,6a]]-1,2,3,4,5,6-hexahydro-2,6-methano-1,3-benzodiazocin-8-ol, S-α-methylbenzylcarbamate salicylate.

31. A pharmaceutical composition which comprises a compound as defined in claim 1 present in an amount effective for alleviating a memory dysfunction characterized by decreased cholinergic function, and a suitable carrier therefor.

32. A method of alleviating in a patient a memory dysfunction characterized by decreased cholinergic function which comprises administering to the patient an effective amount of a compound as defined in claim 1.

* * * * *